United States Patent
Jhan et al.

(10) Patent No.: US 9,364,545 B2
(45) Date of Patent: Jun. 14, 2016

(54) THERMOSENSITIVE INJECTABLE HYDROGEL FOR DRUG DELIVERY

(71) Applicant: Taipei Medical University, Taipei (TW)

(72) Inventors: Hua-Jing Jhan, Taipei (TW); Hsiu-O Ho, Taipei (TW); Ming-Thau Sheu, Taipei (TW); Shing Chuan Shen, Taipei (TW); Yuan Soon Ho, Taipei (TW); Jun-Jen Liu, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 14/309,266

(22) Filed: Jun. 19, 2014

(65) Prior Publication Data

US 2015/0366975 A1    Dec. 24, 2015

(51) Int. Cl.
| | |
|---|---|
| *A61K 31/337* | (2006.01) |
| *A61K 31/704* | (2006.01) |
| *A61K 47/34* | (2006.01) |
| *A61K 47/36* | (2006.01) |
| *A61K 9/06* | (2006.01) |

(52) U.S. Cl.
CPC . *A61K 47/36* (2013.01); *A61K 9/06* (2013.01); *A61K 31/337* (2013.01); *A61K 31/704* (2013.01); *A61K 47/34* (2013.01)

(58) Field of Classification Search
None
See application file for complete search history.

(56) References Cited

U.S. PATENT DOCUMENTS

| | | |
|---|---|---|
| 2012/0100103 A1 | 4/2012 | Park et al. |
| 2014/0005306 A1* | 1/2014 | Rafailovich et al. ............ 524/18 |
| 2014/0065226 A1 | 3/2014 | Brey et al. |

OTHER PUBLICATIONS

Chen, Langmuir 2013, 29, 3721-3729, published Feb. 26, 2013.*
Peter Gibbs et al., A pilot human evaluation of a formulation of irinotecan and hyaluronic acid in 5-fluorouracil-refractory metastatic colorectal cancer patients, Chemotherapy, 55 (2009) 49-59.
Shuang Cai et al., Localized doxorubicin chemotherapy with a biopolymeric nanocarrier improves survival and reduces toxicity in xenografts of human breast cancer, Journal of controlled release : official journal of the Controlled Release Society, 146 (2010) 212-218.
Yu-Li Lo et al., pH-and thermo-sensitive pluronic/poly(acrylic acid) in situ hydrogels for sustained release of an anticancer drug, J Drug Target, 21 (2013) 54-66.

* cited by examiner

*Primary Examiner* — Layla Berry
(74) *Attorney, Agent, or Firm* — WPAT, P.C., Intellectual Property Attorneys; Anthony King

(57) ABSTRACT

The invention develops a developed a thermosensitive injectable hydrogel based on HA and a copolymer of polyethylene oxide (PEO) and polypropylene oxide (PPO), which has a gel formation temperature from 30° C. to 37° C. The thermosensitive injectable hydrogel of the invention provides a potential drug delivery system that can increase therapeutic efficacy of the drug.

16 Claims, 16 Drawing Sheets

THERMOSENSITIVE INJECTABLE HYDROGEL FOR DRUG DELIVERY

FIELD OF THE INVENTION

The present invention relates to a thermosensitive injectable hydrogel for drug delivery. Particularly, the present invention provides an in situ-forming injectable hydrogel for delivering an anti-cancer drug.

BACKGROUND OF THE INVENTION

Although effective anticancer drugs have high specificity and activity against cancers, most drugs distribute throughout the body and are toxic to neoplastic cells. This dose-limiting toxicity associated with most anticancer drugs constrains their potential therapeutic efficacy, therapeutic efficacy. To minimize adverse effects from higher dosages, drugs can be delivered by formulating them as targetable carriers to increase the concentration at the target site and decrease drug concentrations elsewhere in the body or by giving local/intratumor/peritumor injection.

Hyaluronan has been reported to be an ideal carrier for localizing anticancer drugs. Hyaluronan (HA) is a polysaccharide, of alternating D-glucuronic acid and N-acetyl D-glucosamine, found in the connective tissues of the body and cleared primarily by the lymphatic system (12 to 72 h turnover half-life). Gibbs et al. reported that HA-Irinotecan containing standard doses of irinotecan could be safely administered to patients by infusion through a peripheral vein over 90 min. Comparison to historical irinotecan data suggests HA-Irinotecan may have a greater margin of safety without compromising anticancer activity (P. Gibbs, T. J. Brown, R. Ng, R. Jennens, E. Cinc, M. Pho, M. Michael, R. M. Fox, *A pilot human evaluation of a formulation of irinotecan and hyaluronic acid in 5-fluorouracil-refractory metastatic colorectal cancer patients*, Chemotherapy, 55 (2009) 49-59). Cai et al. also reported that the hyaluronan-doxorubicin nanoconjugate administered subcutaneously 2-3 mm from the tumor margins reduces dose-limiting cardiac toxicity with minimal toxicity observed in normal tissues and dramatically inhibits breast cancer progression in vivo, leading to an increased survival rate. Thus, localized chemotherapy to the breast lymphatics with this nanocarrier may represent an improved strategy for treatment of early stage breast cancers (S. Cai, S. Thati, T. R. Baghy, H. M. Diab, N. M. Davies, M. S. Cohen, M. L., Forrest, *Localized doxorubicin chemotherapy with a biopolymeric nanocarrier improves survival and reduces toxicity in xenografts of human breast cancer*, Journal of controlled release: official journal of the Controlled Release Society, 146 (2010) 212-218).

Injection of thermal reversible hydrogel will lead to the formation of a "depot" at the site of administration that slowly and continuously releases the drug to the tumor and surrounding tissue. This kind of topical or injectable gel for physical targeting has additional advantages over passive or other actively targeted therapies in that it can deliver a drug throughout the tumor regardless of vascular status, thus providing accurate dosing without systemic toxicity. Poloxamer gels have been widely applied in drug delivery since they are relatively easy to manufacture and already widely employed in the pharmaceutical fields as "generally regarded as safe" (GRAS) excipients. Currently, research on this type of thermosensitive hydrogels mainly focuses on poloxamer 407 (Pluronic F-127, Molecular Probes, Inc., Eugene, Oreg.). For localized cancer therapy, intratumoral, peritumoreal, and intravesical injection of thermal sensitive hydrogel composed of Pluronic® F127 (F127) has been proposed (Y. L. Lo, C. Y. Hsu, H. R. Lin, *pH-and thereto-sensitive pluronic/poly(acrylic acid) in situ hydrogels for sustained release of an anticancer drug*, J Drug Target, 21 (2013) 54-66). However, such poloxamer gels for drug delivery applications have substantial drawbacks including the gelation time being too long, limited stability, poor mechanical properties and short residence times due to rapid dissolution once placed in a biological environment.

US 20120100103 relates to an situ-forming injectable hydrogel comprising two or more homogeneous or heterogeneous polymers, which are bonded to each other by a dehydrogenation reaction between phenol or aniline moieties on adjacent polymers. US 20140065226 provides compositions including a thereto-responsive hydrogel and a biocompatible monomer or polymer including an amino acid side chain (i.e., having an amino acid linked to the remainder of the monomer or polymer through its side chain), which has thermo-responsive behavior at physiological temperature and is useful as injectable and topical formulations, particularly for biomedical applications such as localized drug delivery.

Although several thermosensitive injectable hydrogels have been developed, there are no satisfactory thermosensitive injectable hydrogels for localized therapy. Therefore, there is a need for developing an in situ forming hydrogel with superior effects in therapy.

SUMMARY OF THE INVENTION

The invention provides a thermosensitive injectable hydrogel, which has a gel formation temperature from 30° C. to 37° C. and comprises an HA polymer and a copolymer of polyethylene oxide (PEO) and polypropylene oxide (PPO), wherein the amounts of HA and the polymer are 0.005% (w/v) to 0.3% (w/v) and 12% (w/v) to 20% (w/v), respectively.

In one embodiment, the polymers of hyaluronan can range in size from about 5,000 Da to about 20,000,000 Da. Any hyaluronan polymer is useful in the hydrogels disclosed herein with the proviso that the hyaluronan can form hydrogel having a gel formation temperature at 30° C. to 37° C. with the polymer of PEO and PPO.

In one embodiment, the copolymer of PEO and PPO is poly(ethylene oxide-propylene oxide-ethylene oxide) (PEO-PPO-PEO). Examples of the PEO-PPO-PEO copolymers includes Pluronic F68NF, Pluronic F127NF, Pluronic F108NF, Pluronic F38NF and Pluronic F87NF. More preferably, the PEO-PPO-PEO copolymer is Pluronic F127NF.

In one embodiment, the amounts of HA and polymer are about 0.005% (w/v) to about 0.3% (w/v) and about 12% (w/v) to about 20% (w/v), respectively. More preferably, the amount of HA is about 0.005% (w/v) to 0.2% (w/v); and the amount of the copolymer of polyethylene oxide (PEO) and polypropylene oxide (PPO) is about 15% (w/v) to about 18% (w/v).

The composition can be administered in liquid state, such as by injection, to a subject in need of therapy.

In another aspect, the invention provides a drug delivery system, comprising a thermosensitive injectable hydrogel of the invention and an active agent. In another aspect, the invention provides a method for treating or alleviating one or more symptoms of a disease in a subject, comprising administering to a subject in need thereof a drug delivery system of the invention. In one embodiment, the present invention provides localized deposition of a large variety of substances, that if administered by, for example, intravenous methods would cause undesirable systemic effects. This is particularly the case where the substances are toxic in some respect, and the toxicity is to be used for local treatment at a specific trauma site in the body. A typical example would be toxins for the treatment of cancer tumours.

For example, the hydrogel of the invention may have significantly anti-cancer activity to cancer cells. By intratumoral administration, the hydrogel results in efficient growth inhibition of cancer cell. The tumor inhibition rate of the hydrogel is significantly higher than for free anti-cancer drug. The in situ injectable hydrogel of the invention is a drug delivery system that could increase the efficacy of cancer chemotherapy.

DETAILED DESCRIPTION OF THE INVENTION

Figure 1:
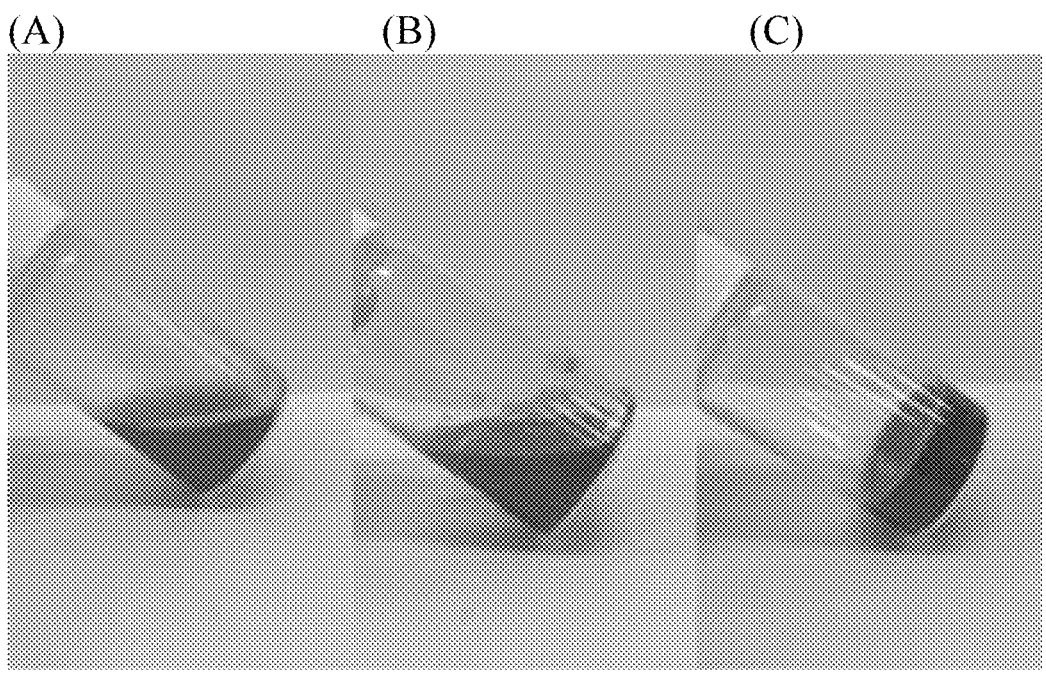
FIG. 1 shows photographs of in vitro sol-gel transition of the DHMF-15 hydrogel upon heating: (A) solution form at 4° C., (B) solution form at 25° C. and (C) gel form at 37° C.

The following description of the invention is provided as an enabling teaching of the invention in its best, currently known embodiment. To this end, those skilled in the relevant art will recognize and appreciate that many changes can be made to the various aspects of the invention described herein while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

The invention develops a thermosensitive injectable hydrogel based on HA and a copolymer of polyethylene oxide (PEO) and polypropylene oxide (PPO), which has a gel formation temperature from 30° C. to 37° C. The thermosensitive injectable hydrogel of the invention provides a drug delivery system that can increase therapeutic efficacy of the drug.

As used throughout, the singular forms "a," "an," and the include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "polymer" as used herein is defined as a compound comprising a linear arrangement of simpler repeating molecules.

The term "hydrogel" as used herein refers to a three-dimensional, hydrophilic or amphiphilic polymeric network capable of taking up large quantities of water. The networks are composed of homopolymers or copolymers, and are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allow them to swell in aqueous media.

The term "crosslinked" as used herein refers to a composition containing intramolecular and/or intermolecular crosslinks, whether arising through covalent or noncovalent bonding. "Noncovalent" bonding includes both hydrogen bonding and electrostatic (ionic) bonding.

The term "temperature sensitive" hydrogel as used herein refers to a block copolymer of the present disclosure and forms, to various degrees, a jelly-like or gelled product when heated to a particular temperature, for example body temperature (37° C.), or a temperature higher than 30° C. The block copolymer is preferably a liquid at room temperature and soluble in water, but upon reaching a particular temperature, forms a hydrogel when mixed with water such that water is a dispersion medium forming the hydrogel.

The term "in situ" as used herein is defined as restricted to a specific site within a body without substantial invasion of surrounding tissues.

The term "active agent" is used herein to refer to a chemical material or compound suitable for administration to a human patient and that induces a desired beneficial effect, e.g., exhibits a desired pharmacological activity. The term includes, for example, agents that are therapeutically effective, prophylactic ally effective, and cosmetically (and cosmeceutically) effective. Also included are derivatives and analogs of those compounds or classes of compounds specifically mentioned which also induce the desired beneficial effect.

In one aspect, the invention provides a thermosensitive injectable hydrogel, which has a gel formation temperature from 30° C. to 37° C. and comprises an HA polymer and a copolymer of polyethylene oxide (PEO) and polypropylene oxide (PPO), wherein the amounts of HA and the polymer are about 0.005% (w/v) to about 0.3% (w/v) and 12% (w/v) to 20% (w/v), respectively.

As used herein, the term "HA polymer" is synonymous with "hyaluronic acid polymer," "hyaluronic acid polymer," and "hyaluronate polymer," which refers to an anionic, non-sulfated glycosaminoglycan polymer comprising disaccharide units, which themselves include D-glucuronic acid and D-N-acetylglucosamine monomers, linked together via alternating beta-1,4 and beta-1,3 glycosidic bonds and pharmaceutically acceptable salts thereof. Hyaluronan polymers can be purified from animal and non-animal sources. Polymers of hyaluronan can range in size from about 5,000 Da to about 2500,000 Da. Any hyaluronan polymer is useful in the hydrogels disclosed herein with the proviso that the hyaluronan can form hydrogel having a gel formation temperature at 30° C. to 37° C. with the polymer of PEO and PPO. The "high molecular weight" HA refers to hyaluronan polymers having a mean molecular weight of 1,000,000 Da or greater. Non-limiting examples of a high molecular weight hyaluronan polymers include hyaluronan polymers about 1,500,000 Da, about 2,000,000 Da, about 2,500,000 Da, about 3,000,000 Da, about 3,500,000 Da, about 4,000,000 Da, about 4,500,000 Da, and about 5,000,000 Da. The "low molecular weight" HA refers to hyaluronan polymers having mean molecular weight of less than 1,000,000 Da. Non-limiting examples of low molecular weight hyaluronan polymers include hyaluronan polymers of about 5,000 Da, about 9,000 Da, about 50,000 Da, about 700,000 Da, about 1500,000 Da, about 2000,000 Da and about 2200,000 Da. Preferably, the molecular weight of hyaluronan polymer ranges from about 9,000 Da to about 25000,000 Da, about 9,000 Da to about 25000,000 Da, about 9,000 Da to about 22000,000 Da, about 9,000 Da to about 15000,000 Da, about 9,000 Da to about 700,000 Da, about 9,000 Da to about 50,000 Da, about 50,000 Da to about 700,000 Da, about 700,000 Da to about 1,500,000 Da, about 700,000 Da to about 2,200,000 Da, about 700,000 Da to about 2,500,000 Da, about 1500,000 Da to about 2,500,000 Da. More preferably, the molecular weight of hyaluronan polymer is about 1500,000 Da to about 2500,000 Da or about 1500,000 Da to about 2200,000 Da.

Block copolymers of ethylene oxide and propylene oxide are relatively non-toxic and non-irritating. Preferred polymers for use in hydrogels of the invention include block copolymers of ethylene oxide and propylene oxide. In one embodiment, the copolymer of PEO and PPO is poly(ethylene oxide-propylene oxide-ethylene oxide) (PEO-PPO-PEO). Examples of the PEO-PPO-PEO copolymers include Pluronic F68NF (sold by BASF) (the molecular weight of this block copolymer is 8400 with 80% of ethylene oxide and 20% of propylene oxide); Pluronic F127NF (the molecular weight of this block copolymer is 12600 with 70% of ethylene oxide and 30% of propylene oxide); Pluronic F108NF (the molecular weight of this block copolymer is 14600 with 80% of ethylene oxide and 20% of propylene oxide); Pluronic F38NF (the molecular weight of this block copolymer is 4700 with 80% of ethylene oxide and 20% of propylene oxide); Pluronic F87NF (the molecular weight of this block copolymer is 8400 with 70% of ethylene oxide and 30% of propylene oxide). More preferably, the PEO-PPO-PEO copolymer is Pluronic F127NF.

In one embodiment, the combination of HA polymer and a copolymer of polyethylene oxide (PEO) and polypropylene oxide (PPO) has a gel formation temperature from 30° C. to 37° C. In one embodiment, the amounts of HA and polymer are about 0.005% (w/v) to about 0.3% (w/v) and about 12% (w/v) to about 20% (w/v), respectively. More preferably, the amount of HA is about 0.005% (w/v) to 0.2% (w/v); and the amount of the copolymer of polyethylene oxide (PEO) and polypropylene oxide (PPO) is about 15% (w/v) to about 18% (w/v). In the above embodiments, more preferably, the amount of HA is about 0.01% (w/v) to about 0.2% (w/v) or 0.01% (w/v) to about 0.2% (w/v); more preferably, the amount of HA is 0.01% (w/v), 0.025% (w/v), 0.075% (w/v), 0.1% (w/v). 0.125% (w/v) or 0.15% (w/v). In the above embodiments, more preferably, the amount of the copolymer of PEO and PPO is about 15% (w/v) to 17.5% (w/v); more preferably, the amount of the copolymer of PEO and PPO is about 15% (w/v), about 16.25% (w/v) or 17.5% (w/v).

In several embodiments, the composition of the invention comprises about 0.01% (w/v) of HA and about 15% (w/v) of the copolymer of PEO and PPO, about 0.025% (w/v) of HA and 15% (w/v) or 16.25% (w/v) of the copolymer of PEO and PPO, about 0.05% (w/v) of HA and about 15% (w/v) or about 16.25% (w/v) of the copolymer of PEO and PPO, about 0.075% (w/v) of HA and about 15% (w/v) or about 16.25% (w/v) of the copolymer of PEO and PPO, about 0.1% (w/v) of HA and about 15% (w/v) or about 16.25% (w/v) of the copolymer of PEO and PPO, about 0.125% (w/v) of HA and about 16.25% (w/v) of HA or about 17.5% (w/v) of the copolymer of PEO and PPO, or about 0.15% (w/v) of HA and about 17.5 (w/v) of the copolymer of PEO and PPO. In these embodiments, preferably, the copolymer of PEO and PPO is PF127.

The composition can be administered in liquid state, such as by injection, to a subject in need of therapy. Either before or after administration, cross-linking can be induced (initiated) in the cross-linkable units, whereby the composition can form a hydrogel. In one embodiment of the invention, a method of administering a hydrogel composition to provide therapy to a site in need thereof includes providing a hydrogel-forming composition as described, administering said hydrogel-forming composition to the site, and initiating cross-linking of said hydrogel-forming composition by body temperature to form a hydrogel. The thermosensitive injectable hydrogel can be used for intratumoral injection, subcutaneous injection, oral delivery, ocular delivery, transdermal, ophthalmic, wound healing, intraperitoneal injection, gene delivery, tissue engineering, colon specific drug delivery.

In another aspect, the invention provides a drug delivery system, comprising a thermosensitive injectable hydrogel of the invention and an active agent. In another aspect, the invention provides a method for treating or alleviating one or more symptoms of a disease in a subject, comprising administering to a subject in need thereof a drug delivery system of the invention. Preferably, the disease is an cancer or wound. Preferably, the delivery is intratumoral injection, subcutaneous injection, oral delivery, ocular delivery, transdermal delivery, ophthalmic delivery, topical delivery, intraperitoneal injection, gene delivery or colon specific drug delivery.

The composition can also include any pharmaceutically active agent useful in treating physiological conditions. The active agent can be any substance that can be released from the composition to treat an undesirable physiological condition. The indication to be treated determines the active agent to be administered. The active agent includes, but is not limited to, a wound hearing agent, an anticancer drug, a radionuclide, a gene therapy composition, a hormone, a nutriceutical, an antibiotic, an anti-inflammatory agent, an antiviral agent, an antibacterial agent and a combination thereof. In one embodiment, the present invention provides localized deposition of a large variety of substances, that if administered by, for example, intravenous methods would cause undesirable systemic effects. This is particularly the case where the substances are toxic in some respect, and the toxicity is to be used for local treatment at a specific trauma site in the body. A typical example would be toxins for the treatment of, for example, cancer tumours. Particular examples of antibiotics include an antibiotic selected from the group consisting of tetracycline, minocycline, doxycycline, ofloxacin, revofloxacin, ciprofloxacin, clarithromycin, erythromycin, cefaclor, cefotaxim, imipenem, penicillin, gentamycin, streptomycin, bancomycin, or a derivative or mixture thereof. Particular examples of anti-cancer agents include methotrexate, carboplatin, taxol, cisplatin, 5-fluorouracil, doxorubicin, etpocide, paclitaxel, docetaxel, camtotecin, cytosine, arabinose, and derivatives and mixtures thereof. Particular examples of anti-inflammatory agents include an anti-inflammatory agent selected from the group consisting of indometacin, ibuprofen, ketoprofen, piroxicam, flubiprofen, diclofenac, and derivatives and mixtures thereof. Particular examples of anti-viral agents include an anti-viral agent selected from the group consisting of acyclovir, robavin, and derivatives and mixtures thereof. Particular examples of antibacterial agents include an antibacterial agent selected from the group consisting of ketoconazole, itraconazole, fluconazole, amphotericin-B, griceofulvin, and derivatives and mixtures thereof.

For example, the hydrogel of the invention has significant anti-cancer activity to cancer cells. By intratumoral administration, the hydrogel results in efficient growth inhibition of cancer cell. The tumor inhibition rate of the hydrogel is significantly higher than for free anti-cancer drug. The in situ injectable hydrogel of the invention is a drug delivery system that could increase the efficacy of cancer chemotherapy.

Reference will now be made in detail to the preferred embodiments of the present invention. However, the following examples and comparative examples are illustrative only, and the scope of the present invention is not limited thereto

EXAMPLES

Materials

Hyaluronic acid FCH-80, a high molecular weight (e.g., about $1.5-2.2 \times 10^6$ MW), was purchased from Foodchemifa Co., Ltd (Tokyo, Japan), Doxorubicin Hydrochloride was purchased from Zhejiang Hisun Pharmaceutical Co. Ltd. (Zhejiang, China), magnesium chloride, regenerated cellulose tubular membrane (Cellu•Sep T2, Nominal MWCO: 6,000~8,000, Membrane Filtration Products, Inc., Texas, USA), and all reagents were obtained from Sigma-Aldrich Co. (ST. Louis, Mo., USA). Kolliphor P407 was purchased from BASF (Ludwigshafen, Germany). Fetal bovine serum, FBS was obtained from Biowest (Nuaillé, France). Male Balb/c mice were purchased from BioLASCO Taiwan Co., Ltd (Taipei, Taiwan). All other chemicals were analytical grade and used without further purification.

Example 1

Preparation of Dox Loaded in Thermosensitive Hydrogel

The thermosensitive Dox/HA hydrogel was prepared by a physical mixing method as follows: deionized water, 1% HA solution, 1 M $MgCl_2$ solution and 30% PF127 were mixing together in the tube and put it at ice bath for 30 mins. The mixture was then mechanically vortexed at 2000 rpm (1/min) by IKA MS1 minishaker (IKA, Germany) and 10 mg/mL Dox solution was slowly added.

Example 2

Comparative Studies of Gel-Forming of Thermosensitive Hydrogel Formulations

In preformulation studies, the formulation DHMF-0 (no PF107 contained) formed gel state at 4° C. and formed solution state at 37° C. It cannot be used for administration by injection. It will be a solution form before being injected into the body and gel form after entering the body.

In order to improve gel-forming ability, PF127 polymer was added to change the physical properties of the hydrogel. PF127 was dissolved in distilled water with gentle stirring at 4° C. and put in a refrigerator overnight until a clear solution was formed. PF127 solution was kept in an ice bath to keep it from solidifying. The results are shown in Table 1.

DHMF-0 was gel form at 4° C. while PF127 is solution, so they cannot be mixed together. DHMF-0, DHMF-5 and DHMF-10 are solution forms at 25° C. and also are gel forms at 37° C., so the three formulations cannot by administered to human body by injection. Although DHMF-20 is gel form at 37° C., it is also gel form at 25° C. and thus cannot be used in in situ administered by injection.

The optimum formulation of the invention is DHMF-15, it is solution form at 25° C. and gel form at 37° C. The compositions of DHMF-15 are 1 mg/mL Dox, 0.1% HA, 0.1 M magnesium chloride and 0.15 mg/mL PF127. The order in which they are added is a critical process in our studies. DHMF-15 formulation is prepared by mixing HA, $MgCl_2$ and PF127 and then adding Dox solution with continue vortex. The optimum formulation, DHMF-15, contains 1 mg/mL Dox, 0.1% HA, and 0.1 M magnesium chloride, which was predicted by $n_o$ precipitation, assay, and stability of formulation.

The control formulation is DMF-15 hydrogel and DF-15 hydrogel. DMF-15 hydrogel contains Dox, $MgCl_2$ and PF127. DMF-15 hydrogel without added HA and it can be used to explore HA function. DF-15 hydrogel contains Dox and PF127. DF-15 hydrogel without added HA and $MgCl_2$ and it demonstrates Dox loading in PF127.

The in situ gelation of the DHMF-15 formulation is shown in FIG. 1. It was clearly observed that DHMF-15 formulation exhibited solution state at 4° C. and 25° C. (FIG. 1A and FIG. 1B.) and it transformed into gel state in 1 min at 37° C. (FIG. 1C.). The results demonstrated DHMF-15 formulation is injectable.

TABLE 1

Effect of PF127 content on the morphology at 4° C., 25° C., and 37° C.

| Acronyms | Doxorubicin (mg/mL) | HA (%) | $MgCl_2$ (M) | PF127 (mg/mL) | Temperature | | |
|---|---|---|---|---|---|---|---|
| | | | | | 4° C. | 25° C. | 37° C. |
| DHMF-0 | 1 | 0.1 | 0.1 | 0 | Gel | Solution | Solution |
| DHMF-5 | 1 | 0.1 | 0.1 | 0.05 | Gel | Solution | Solution |
| DHMF-10 | 1 | 0.1 | 0.1 | 0.10 | Solution | Solution | Solution |
| DHMF-15 | 1 | 0.1 | 0.1 | 0.15 | Solution | Solution | Gel |
| DHMF-20 | 1 | 0.1 | 0.1 | 0.20 | Solution | Gel | Gel |
| DMF-15 (Control) | 1 | 0 | 0.1 | 0.15 | Solution | Solution | Gel |
| DF-15 (Control) | 1 | 0 | 0 | 0.15 | Solution | Solution | Gel |

Other formations with various contents of HA and PF127 were prepared; their morphology at 4° C., 25° C., and 37° C. are illustrated in Table 2.

| HA (%) | PF127 (%) | Temperature | |
|---|---|---|---|
| | | 25° C. | 37° C. |
| 0.010 | 15.00 | Solution | Gel |
| 0.025 | 15.00 | Solution | Gel |
| | 16.25 | | |
| 0.05 | 15.00 | Solution | Gel |
| | 16.25 | | |
| 0.075 | 15.00 | Solution | Gel |
| | 16.25 | | |
| 0.100 | 15.00 | Solution | Gel |
| | 16.25 | | |
| 0.125 | 16.25 | Solution | Gel |
| | 17.50 | | |
| 0.150 | 17.50 | Solution | Gel |

Example 2

Characterization of Hydrogel

Rheological Characterization

The rheological parameters were measured by a rheometer (HAAKE Rotation Rheometer RS-1, Germany). The test method employed was dynamic temperature ramp. The rheological parameters changing with temperature were measured at a fixed frequency of 1 Hz in the temperature range of 15-60° C. at heating rate of 1.5° C./min (Q. Wang, H. B. Xu, X. L. Yang, Y. J. Yang, *Rheological Study of Aqueous Dispersions of In Situ Gelable Thermosensitive Polymer Nanogels*, Polym Eng Sci, 49 (2009) 177-181).

Sol-Gel Transition Phase Diagram

The sol-gel phase transition temperature for Dox/HA hydrogels and PF127 were determined using the test tube inverting method in a 15 ml test tube with a temperature increment of 2° C./step. The sol-gel transition was visually observed by inverting the tube, and the gel state was determined by inverting the test tube when no fluidity was visually observed in 1 min.

Figure 2:
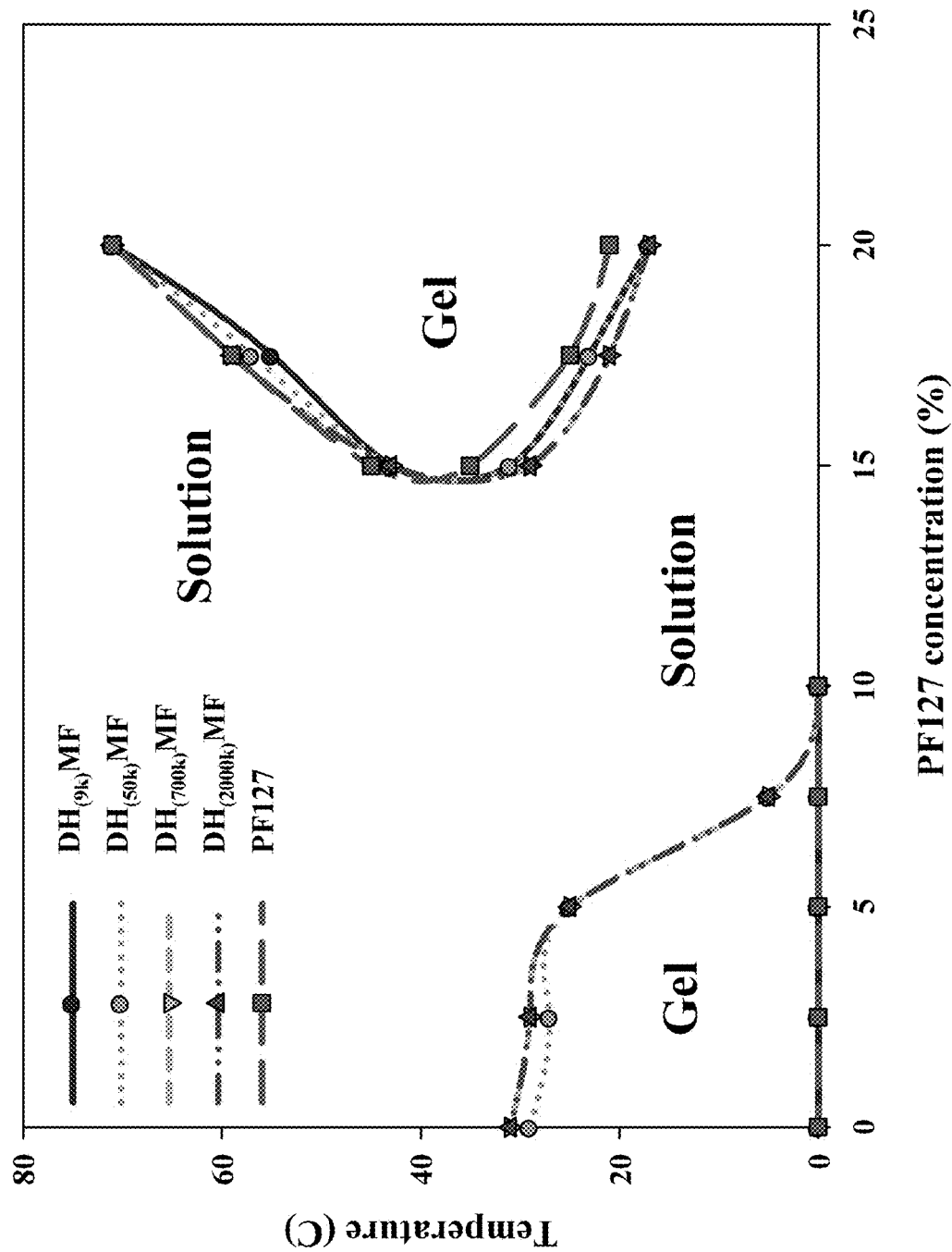
FIG. 2 shows sol-gel phase transition diagram of Dox/HA/ $MgCl_2$ with various PF127 concentrations.
Figure 3:
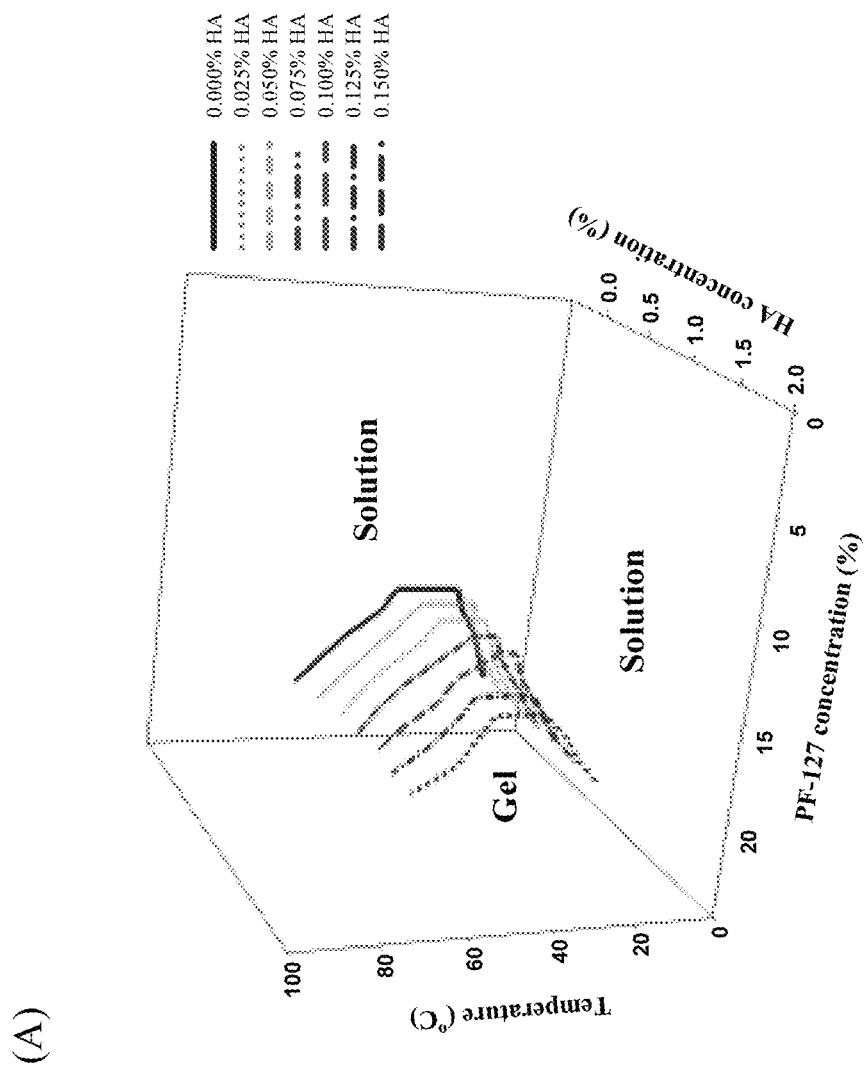
FIG. 3 shows the physical properties of injectable formulation is liquid at room temperature but turns into gel form when injected into the body (around 37° C.).
Figure 3:
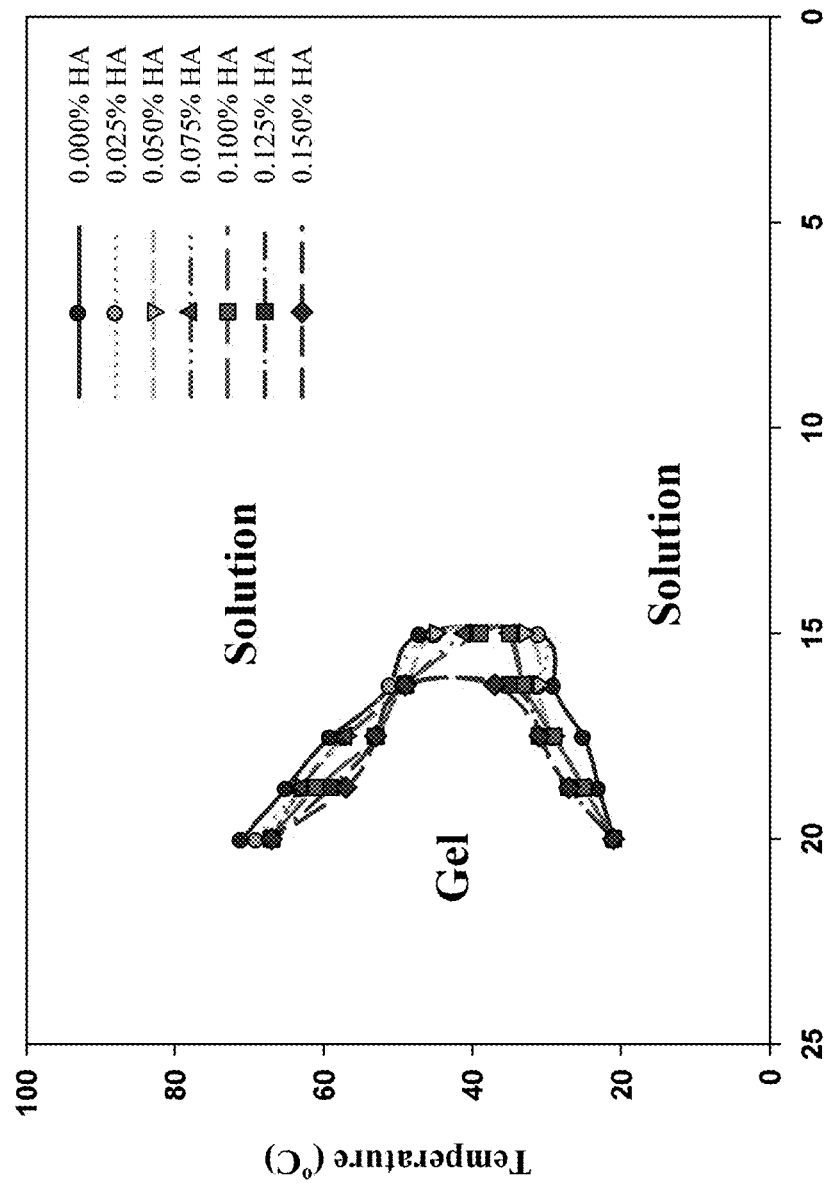

As shown in FIG. 2, the DHMF-15 hydrogel displayed a different sol-gel phase transition curves compare to PF127. PF127 was found to form a gel at a concentration of 17.5% at 25° C., the solution behaves as a mobile viscous liquid at 25° C. (room temperature) and it is a semisolid transparent gel at 37° C. (body temperature). The right-shifter sol-gel transition curves of DHMF-15 hydrogel, in which the lower critical gelation temperature (LCGT) was lower than PF127, demonstrates the formulation containing HA and $MgCl_2$ will decrease the LCGT. The left-shifter sol-gel transition curves of DHMF-15 hydrogel shows gel state in the low concentration of PF127, which is different than other studies that employed PF127 as polymer. The hydrogel was formed in a lower temperature when Dox on HA chains made coordinated bonds through metal chelation. The in situ gelation of the formulations of Table 2 are shown in FIG. 3. The physical properties of the injectable formulation is liquid at room temperature turning into gel form when injected into the body (around 37° C.). The suitable gelation temperature range of optimum formulation is between 30 and 35° C. The gelation temperature of DHMF-015 formulation is 33° C., which is suitable for an be injectable formulation.

In Vivo Hydrogel Formation

To investigate the properties required as an injectable formulation, an aqueous solution (100 μl) of Dox/HA hydrogel was injected subcutaneously into the backs of male Balb/c mice. After 5 min, the mice were sacrificed and the gel morphology was observed.

Figure 4:
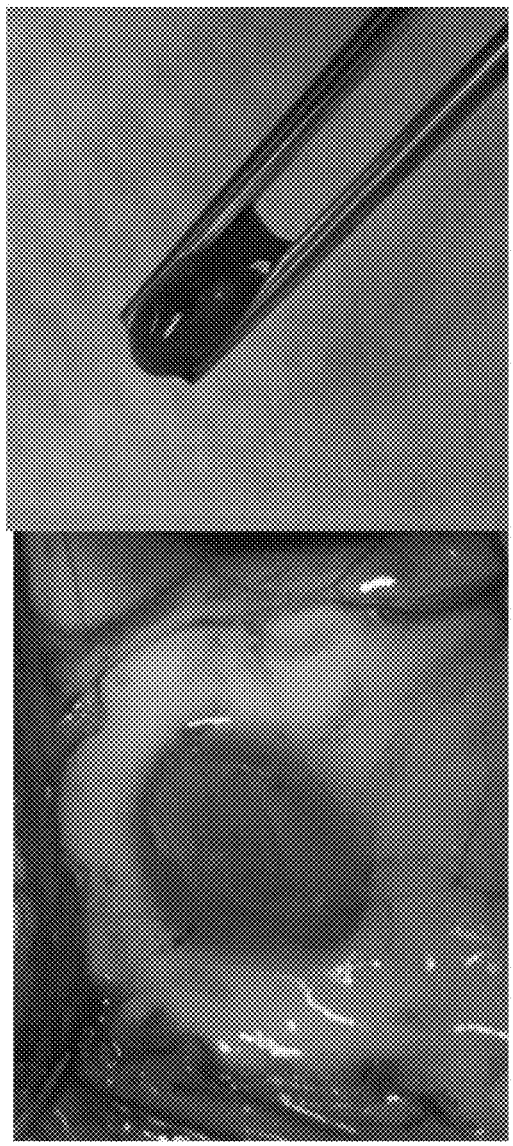
FIG. 4 shows photographs of in situ dox hydrogel formation 5 min after subcutaneous injection of DHMF-15 solution into male Balb/c mice.

The thermosensitive hydrogels were injectable with syringe at room temperature of 25° C. In addition to the physical and chemical properties of DHMF-15 hydrogel, the injectable properties and in vivo gelation were studied by injection into an animal body. One hundred microliter DHMF-15 solution at RT was subcutaneously injected into the back of male mice. The mouse was sacrificed and morphology of the gel was observed 5 min after the injection. As shown in FIG. 4, a red hydrogel contains Dox formed in situ in a short time as a result of the temperature changes caused by the mouse's body condition. According to the results, we can demonstrate the DHMF-15 hydrogel is an injectable formulation at RT and rapidly forms a hydrogel upon injection into the body site.

Scanning Electron Microscopy (SEM) Observation

The morphology of Dox/HA hydrogels was observed by scanning electron microscopy (Hitachi S-2400). The freeze-dried sample of Dox/HA hydrogels was cut-off with treatment of liquid nitrogen followed by sputtering with gold before observation.

Figure 5:
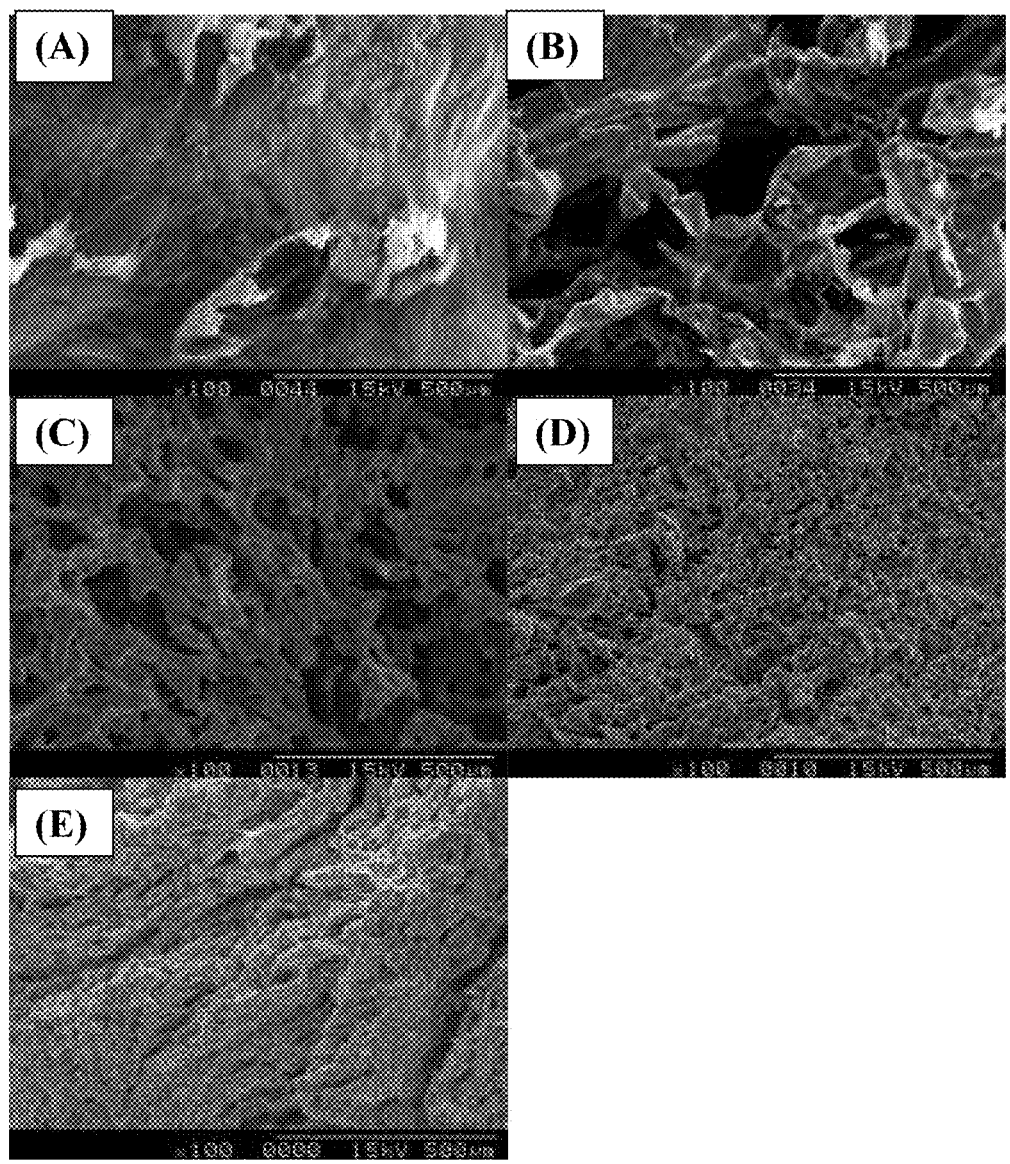
FIG. 5 shows SEM photographs of Dox, HA and $MgCl_2$ mixed with various concentrations of PF127 (A) DHMF-0; (B) DHMF-5; (C) DHMF-10; (D) DHMF-15; (E) DHMF-20.

The hydrogels were frozen at −80° C. and lyophilized, and sectioned for SEM analysis. FIG. 5 represents the SEM images of Dox hydrogels derived from various concentrations of PF-127 (0-0.2 mg/mL; w/v). All hydrogels showed a porous network with different pore size. Interconnected pores were also widely distributed in the hydrogel. Compared with DHMF-0 formulation, the others show a less porous structure; DHMF-0 formulation is smoother than the others (see FIG. 5A). However, DHMF-20 exhibits a smaller pore size compared to DHMF-0. The structure of DHMF-20 is more compact and rigid. Higher concentration of PF-127 leads to a more compact microstructure.

In Vitro Drug Release Studies

Drug release profiles of hydrogel of Dox were determined by dialysis. One milliliter of the hydrogel was placed in regenerated cellulose tubular membrane. The sample in the dialysis bag was immersed in 20 mL pre-warmed phosphate buffers of different pH values (pH 3.0~7.0, and pH 5.8~7.4, 37±0.1° C.) and placed it in the water bath maintained in a shaker at 37±0.1° C. with 100 rpm. In order to maintain sink condition, at predetermined time intervals, all medium was withdrawn and replaced with an equal volume of fresh medium. All release studies were determined in triplicate. The released amount of doxorubicin was determined by HPLC. The stationary phase was composed of 5 µm particle size C18 column material, packed in a 250*4.6 mm stainless steel column (Discovery®, SUPELCO, Bellefonte, Pa.). The mobile phase consisted of water:acetonitrile:methanol:acetic acid (650:250:100:2, v/v/v/v) adjusted to pH 3.6 with 2N NaOH. The flow rate of the mobile phase was set at 1.0 ml/min. The uv-visible detector was operated at 254 nm. The column oven temperature was maintained at 40° C. Twenty microliters of sample was injected.

Figure 6:
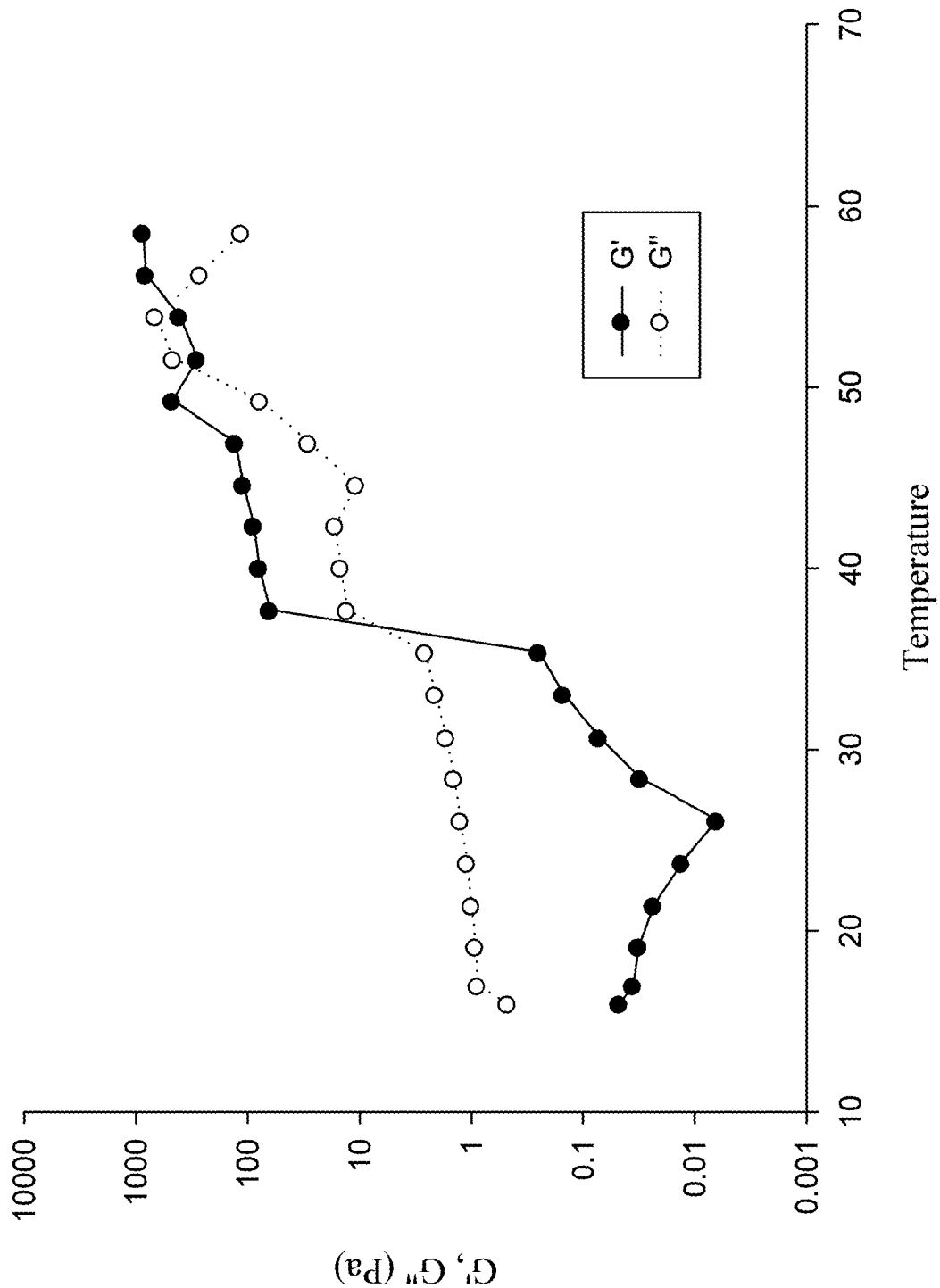
FIG. 6 shows elastic modulus (G') and viscous modulus (G") as a function of temperature of DHMF-15 formulation at a frequency value of 1 Hz.

The mechanical strength and viscoelastic properties of DHMF-15 formulation was investigated by using a rheometer to predict its physical integrity and thermosensitive behavior in vivo. The elastic modulus (G') and viscous modulus (G") of DHMF-15 as a function of temperature, at a frequency value of 1 Hz, is shown in FIG. 6. The gelation temperature ($T_{gel}$) was identified as the temperature at which G' curve and G" curve crossover each other. FIG. 6 shows that the G" is higher than G' for a temperature above 36° C., but G is higher than G" when the temperature is below 36° C. This result demonstrates that the DHMF-15 hydrogel undergoes a temperature-induced transition from a viscoelastic fluid to an elastic hydrogel at a temperature over 36° C. In this study, $T_{gel}$ of DHMF-15 is 36° C., which close to body temperature, so it is suitable as temperature sensitive hydrogel for purpose of the Dox delivery study.

Example 3

In Vitro Dox Release

To evaluate the Dox release mechanism, the results were analyzed using a semiempirical equation $$M_t/M_\infty = kt^n \qquad \text{Eq. (1)}$$

where $M_t/M_\infty$ is the fractional release of the drug at time t, k is a kinetic constant incorporating structural and geometric characteristics of the device, and n is the release exponent, indicative of the drug release mechanism (S. Nie, W. L. Hsiao, W. Pan, Z. Yang, *Thermoreversible Pluronic F127-based hydrogel containing liposomes for the controlled delivery of paclitaxel: in vitro drug release, cell cytotoxicity, and uptake studies, International journal of nanomedicine*, 6 (2011) 151-166; Y. N. Dai, P. Li, J. P. Zhang, A. Q. Wang, Q. Wei, *Swelling characteristics and drug delivery properties of nifedipine-loaded pH sensitive alginate-chitosan hydrogel beads, Journal of biomedical materials research. Part B, Applied biomaterials*, 86 (2008) 493-500).

Figure 7:
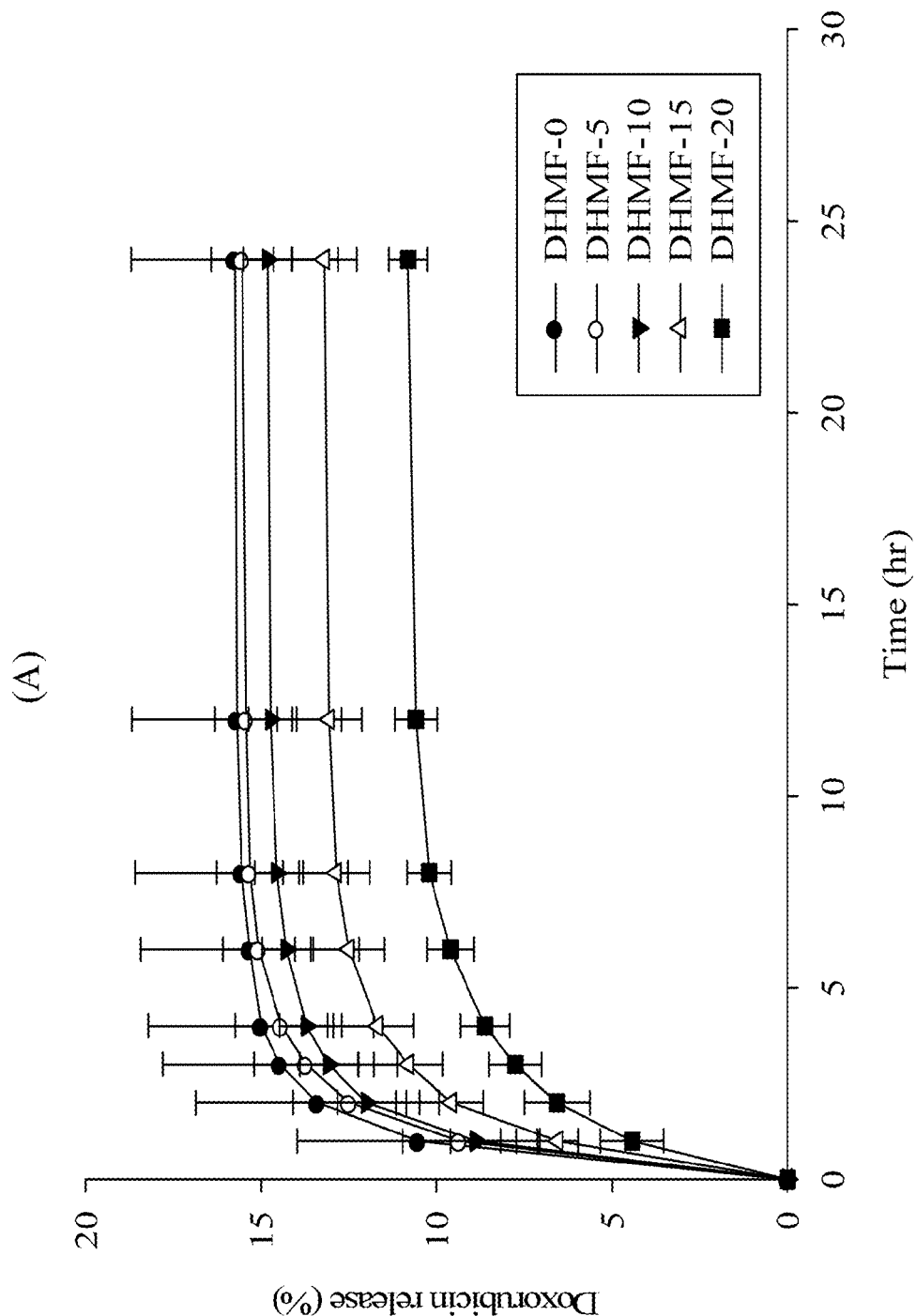
FIG. 7 shows release of Dox from hydrogel in phosphate buffer at 37° C. (A) and depicts the release profiles of Dox from different hydrogel formulations at pH6.8 phosphate buffer. (B) depicts the release profiles of doxorubicin from DHMF-15 hydrogel at phosphate buffers with different pH. (N=3).
Figure 7:
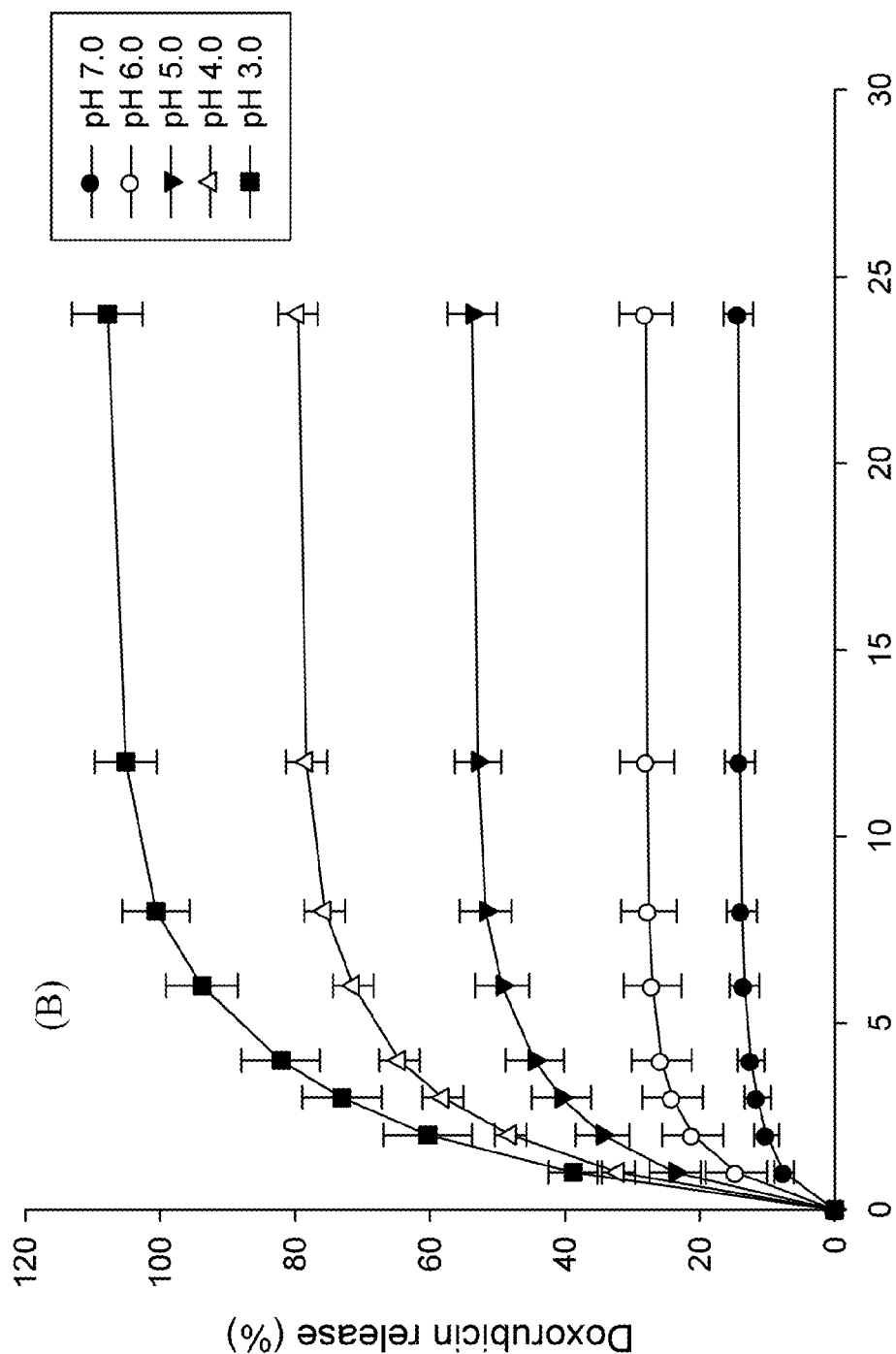

Dox release from thermosensitive hydrogels is displayed in FIG. 7. Dox hydrogels were placed in a dialysis bag that was immersed in 20 ml buffer and Dox released was measured at 37° C. The initial rate of release of doxorubicin is rapid and then slows down after several hours. FIG. 7A illustrates the in vitro release behavior of thermosensitive hydrogel with a different PF-127 amount. The cumulative amount of Dox release from hydrogel without PF127 was about 15.0% within 4 hours. In contrast, that released from the hydrogels contain the PF127 was comparatively low: about 12.4%, 13.7%, 11.7% and 8.6% for DHMF-5, DHMF-10, DHMF-15, DHMF-20, respectively. There are two explanations for this behavior. One is the increased content of PF127 results from the morphology of formulation. DHMF-15 and DHMF-20 were hydrogel form at 37° C., whereas the others were solution form. The Dox was released from solution is faster than from hydrogel. The second reason is the porous structure of hydrogel. According to the SEM observations, the pore size of DHMF-20 is smaller than that of DHMF-0. The results illustrate higher content of PF-127 corresponds to slower release.

The environment of the tumor site is lower pH than that of a normal tissue site. We developed the pH sensitivity hydrogel to use in clinical treatment. The influence of pH values of the phosphate buffer on the drug release at 37° C. is shown in FIG. 7B. As shown in FIG. 7B, Dox release rate was significantly changed according to the environment pH value. The results showed that lower pH value corresponds to faster Dox release rate. The initial burst could lead to immediate suppression of growth of the cancer cells. However, Dox release from DHMF-15 hydrogel is only 11.0% after 24 hours at pH 7.4 PBS, which indicates DHMF-15 didn't release Dox in the normal tissue and to provide protection against damage to a normal cell.

Dox is a weak amphipathic base (pKa 8.3) and HA has a pKa value of about 3.0. The electrostatic interaction between amine group in Dox and carboxylic acid group in HA was only able to dissociate at a lower pH value. This is responsible for the release of Dox from hydrogel increasing with decreasing pH value of medium.

Based on the highest correlation coefficient ($R^2$ value), the results show that the release profile of Dox fits best with the Korsmyer equation ($R^2$=0.7403 0.9946). The Dox release profile was studied when the exponent n from Eq. (1) was calculated. Accordingly, the value of n=0.1888-0.5832 from pH 7.0 to pH 3.0 indicates that both polymer chain relaxation and Fickian diffusion were determinant factors for regulating the Dox release from hydrogel matrix.

Example 4

Cell Viability Studies

C26 colon carcinoma cells and HT29 human colon cancer cells were cultured with RPMI-1640 with 10% fetal bovine serum and 10% penicillinstreptomycin. MCF-7 human breast cancer cells MEM were cultured with Eagle's MEM with 10% fetal bovine serum and 10% penicillinstreptomycin. Cells were seeded at a density of $5 \times 10^4$ cells per well in 24-well plates. After 24 hours of incubation at 37° C. with 5% $CO_2$, the medium was replaced with new medium containing Dox formulation. After 24 hours incubation, cell survival was then measured using tetrazolium salt MTT assay. One hundred microliters of MTT (6 mg/mL) was added to each well for 4 hours. The medium was removed after 3 hours incubation and then 200 µl DMSO was added to dissolve any purple formazan crystal formed. Remove the solvent was removed and dried in an oven at 50° C. for 2 hours. Cell viability was measured by ELISA reader and absorbance set at 520 nm.

Figure 8:
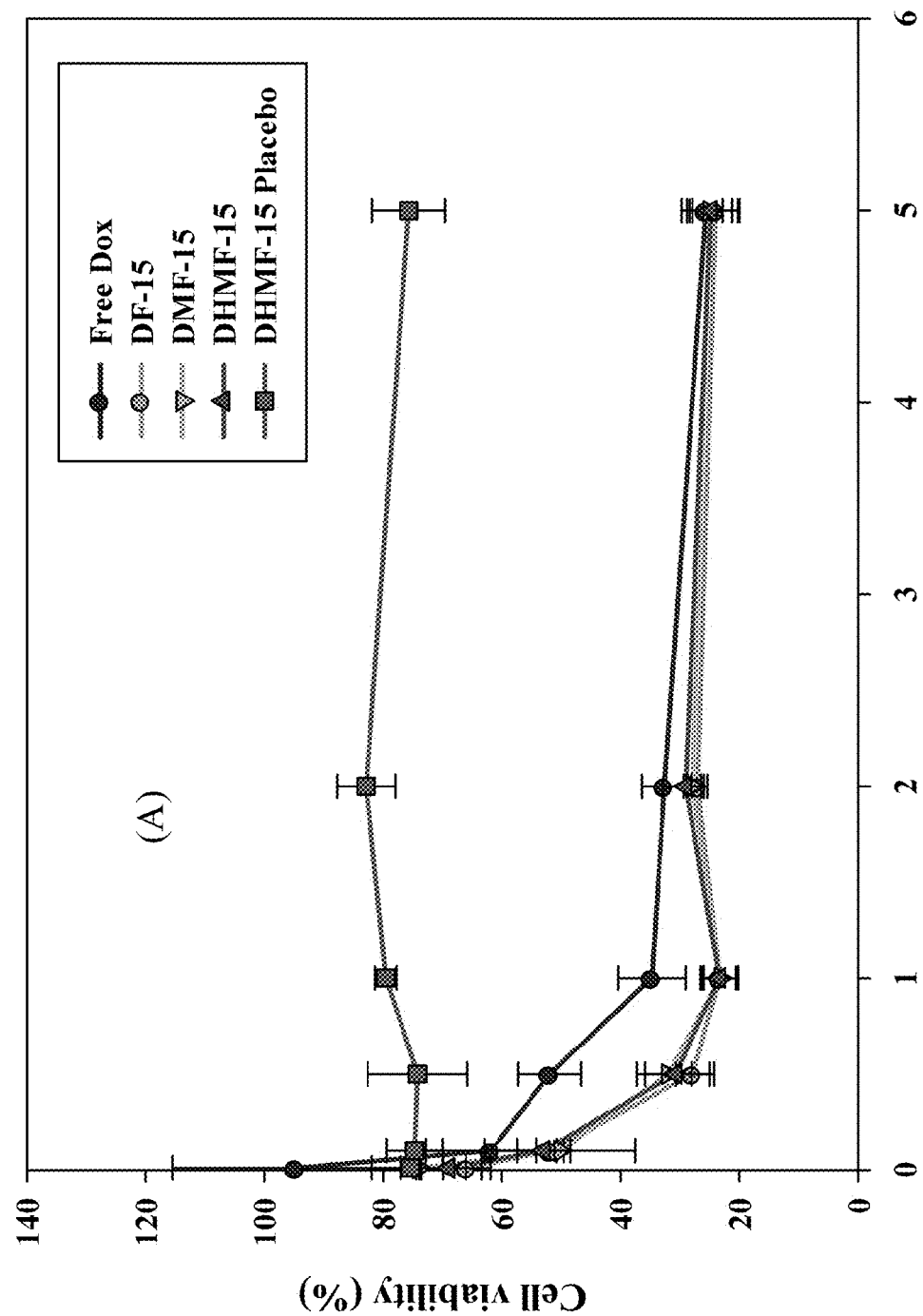
FIG. 8 shows cytotoxicity of Dox/HA hydrogel on cancer cells in vitro studies. DHMF-15 hydrogel, free Dox solution, DHMF-15 placebo against C26 (A), HT29 (B) and MCF7 cells (C) are shown. The cell viability of the different samples was tested using MTT assay after 24 h of incubation. (N=3).
Figure 8:
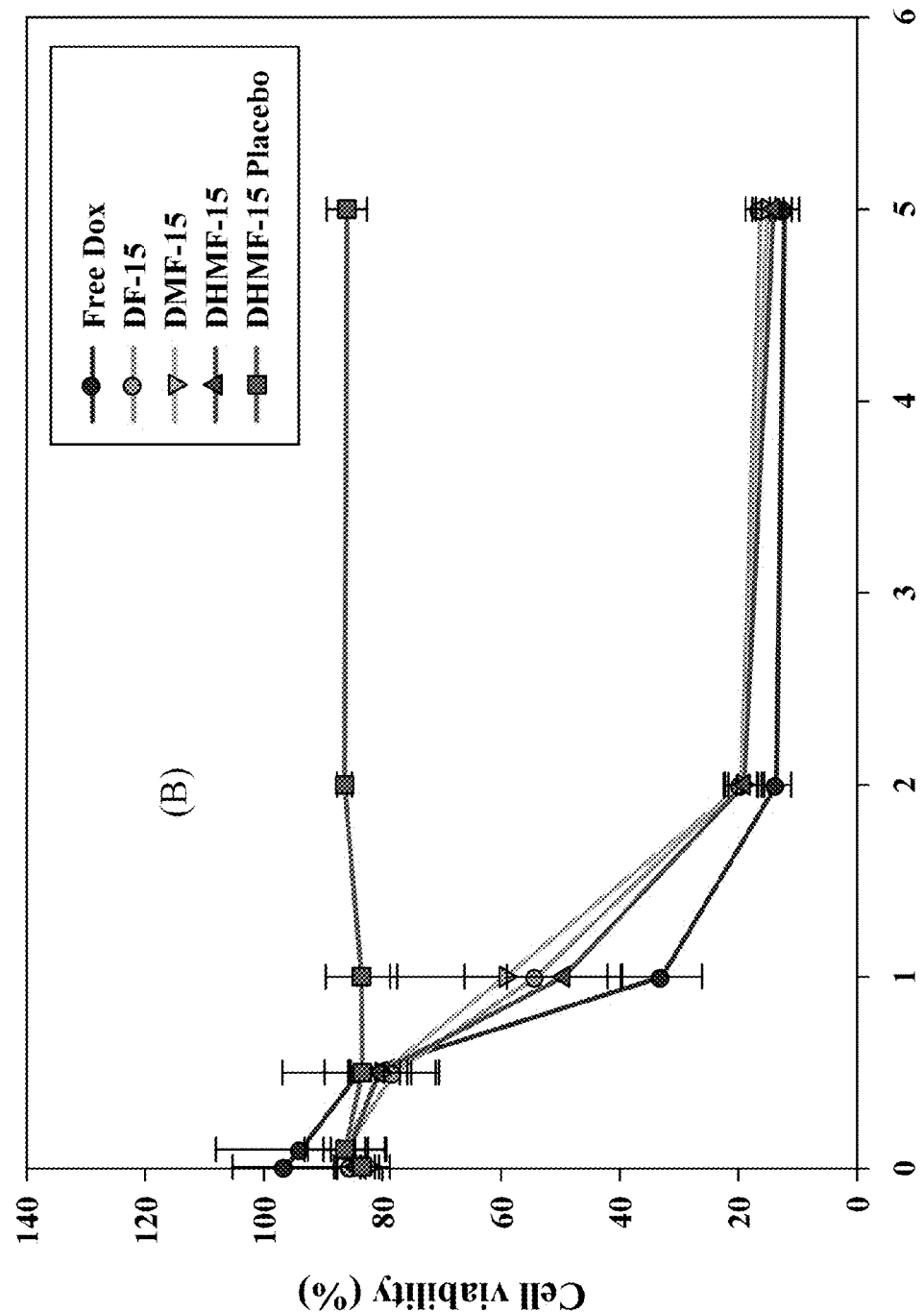
Figure 8:
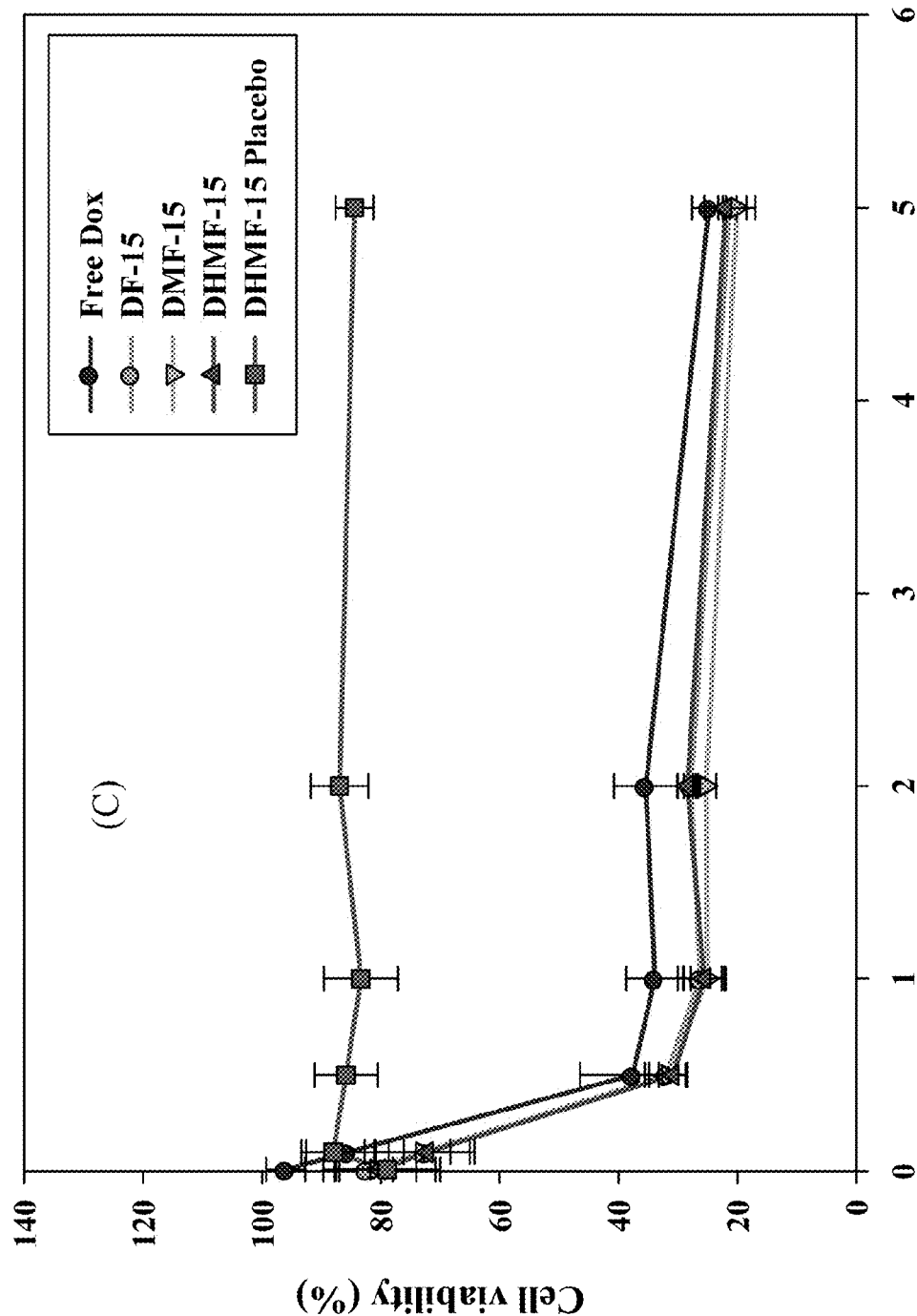

To assess the cellular cytotoxicity of the Dox/HA hydrogel, C26 colon cancer cell, HT29 human colon cancer cell and MCF7 human breast cancer cell lines were used. The MTT assay was used to assess the cell viability studies in vitro. As shown in FIG. 8, the DHMF-15 placebo did not show any cytotoxicity activity in C26, HT29 and MCF7 cells.

It was found that DHMF-15 hydrogel was effective to inhibit the growth of C26, HT29 and MCF7 cells. Free doxorubicin also had potent cytotoxicity toward C26, HT29 and MCF7 cells. In FIG. 8C, a significant difference is seen between DHMF-15 hydrogel and free doxorubicin solution, the cytotoxicity of DHMF-15 hydrogel was stronger than that of free doxorubicin solution in MCF7 cells. MCF7 cells are known to overexpress HA recognizable CD44 receptors on the cell membrane. The results demonstrate that DHMF-15 formulation contains more HA via HA receptor mediated endocytosis than free Dox solution.

Example 5

Tumor Inhibition Studies

The suspension of C16 cells ($1.0 \times 10^6$ cells/100 μl) was injected subcutaneously in the right flank of Balb/c male mice using 26 G needles. After 7 days tumor size reached 100-300 mm$^3$. The C16 tumor bearing mice were randomly divided into three groups (n=3) and received following treatments. Group 1 mice were treated with an intratumoral injection of sterile PBS as control group; Group 2, mice received an intratumoral injection of Dox-HA hydrogel; Group 3, mice received an intratumoral injection of free Dox solution (4 mg/kg in 0.1 mL). The mice were weighed and tumor size was measured using a capliper for 10 days post intratumoral injection. The tumor volume (V) was calculated with the following formula $$V = [\text{length} \times (\text{width})^2]/2$$

On day 10, the mice were sacrificed and the tumor masses harvested, weighted, and photographed. Tumor inhibition rate was calculated using the equation.

$$\text{Tumor inhibition rate (\%)} = (W_c - W_t)/W_c$$

where $W_c$ is the weight of the tumor in the control group and $W_t$ is the weight of the tumor in the test formulation group (L. Chen, X. Sha, X. Jiang, Y. Chen, Q. Ren, X. Fang, *Pluronic P105/F127 mixed micelles for the delivery of docetaxel against Taxol-resistant non-small cell lung cancer: optimization and in vitro, in vivo evaluation, International journal of nanomedicine*, 8 (2013) 73-84).

Figure 9:
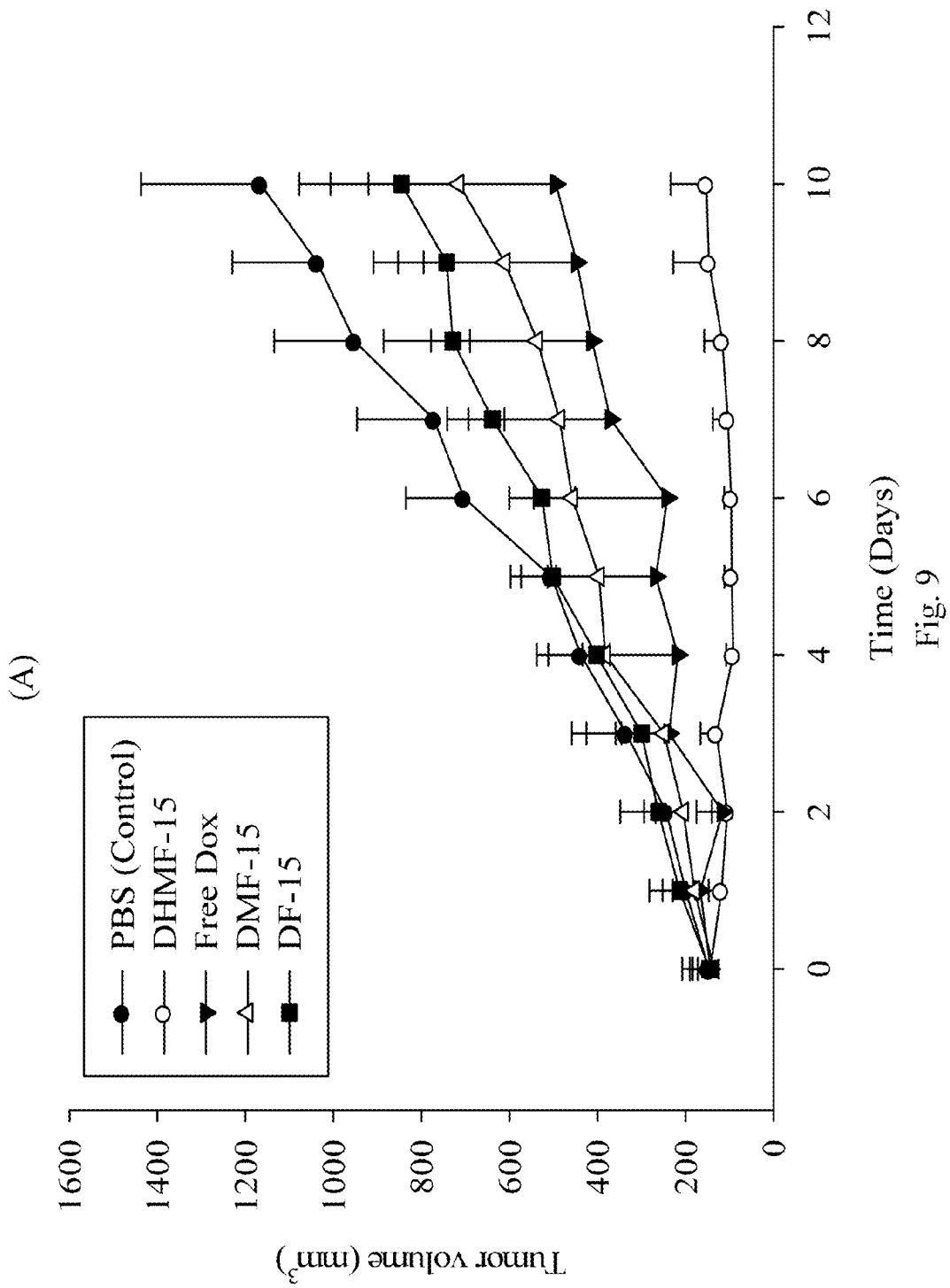
FIG. 9 shows the in vivo antitumor effect of DHMF-15 hydrogel. (A) Changes in tumor volumes; (B) changes in mice body weights; (C) tumor taken out at day 10 post injection; (D) excised tumor weight. PBS is phosphate buffer; free doxorubicin is Dox solution only. (n=3).
Figure 9:
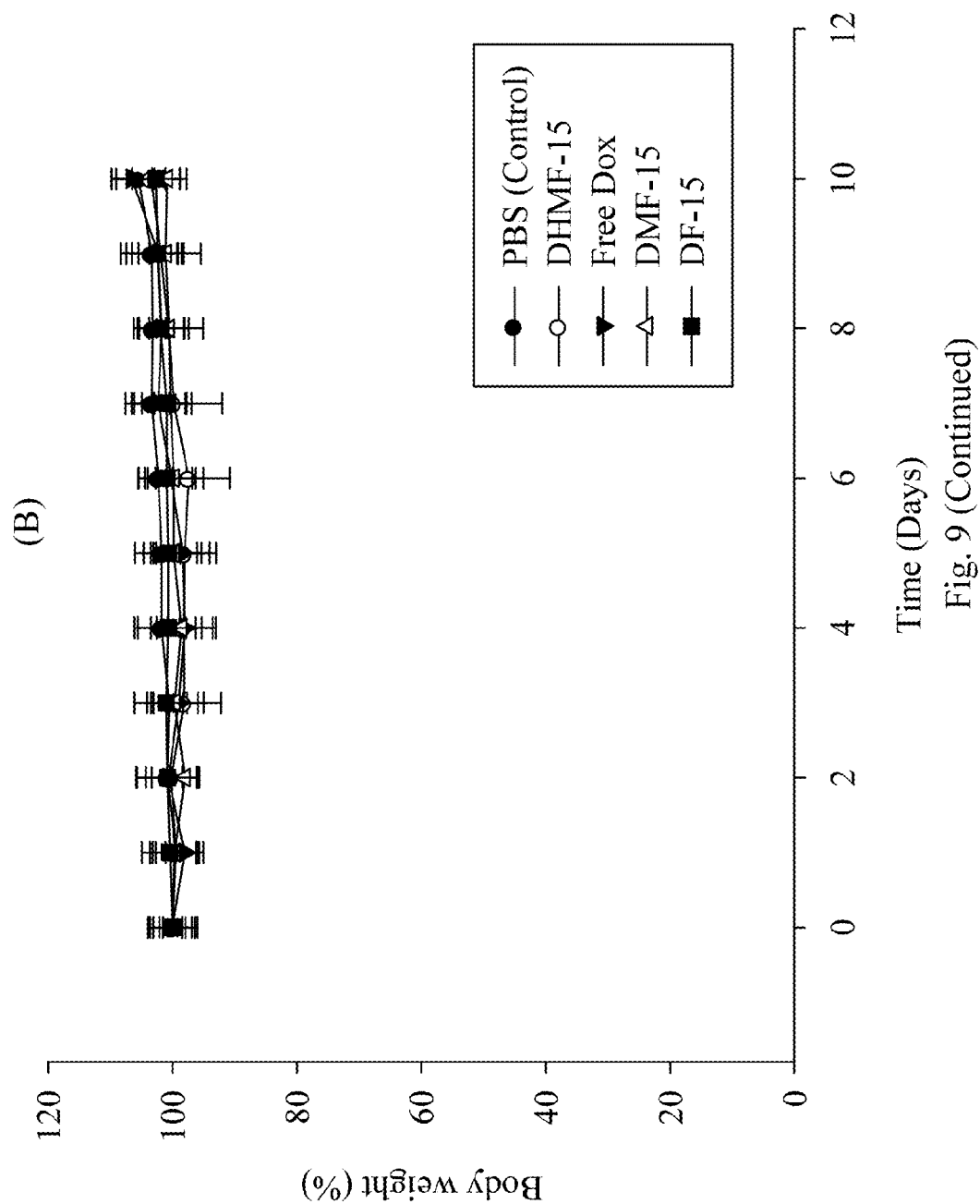
Figure 9:
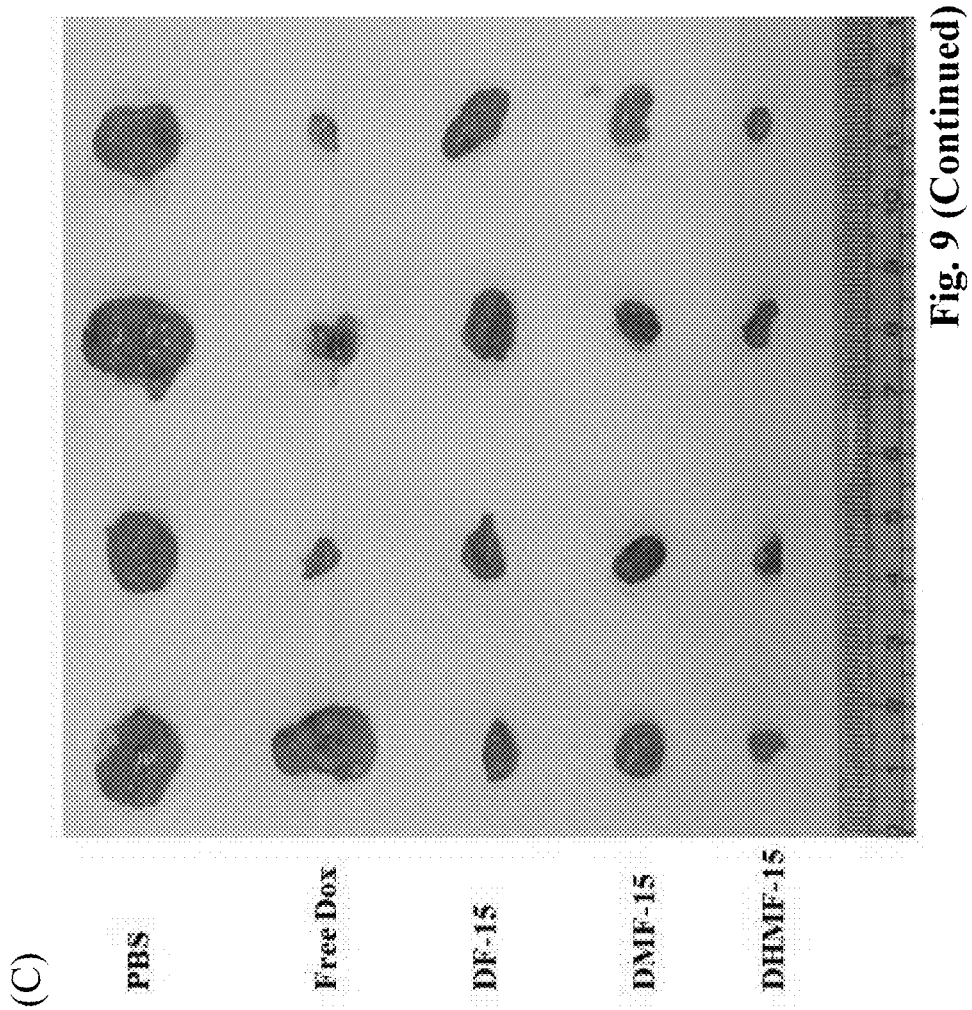
Figure 9:
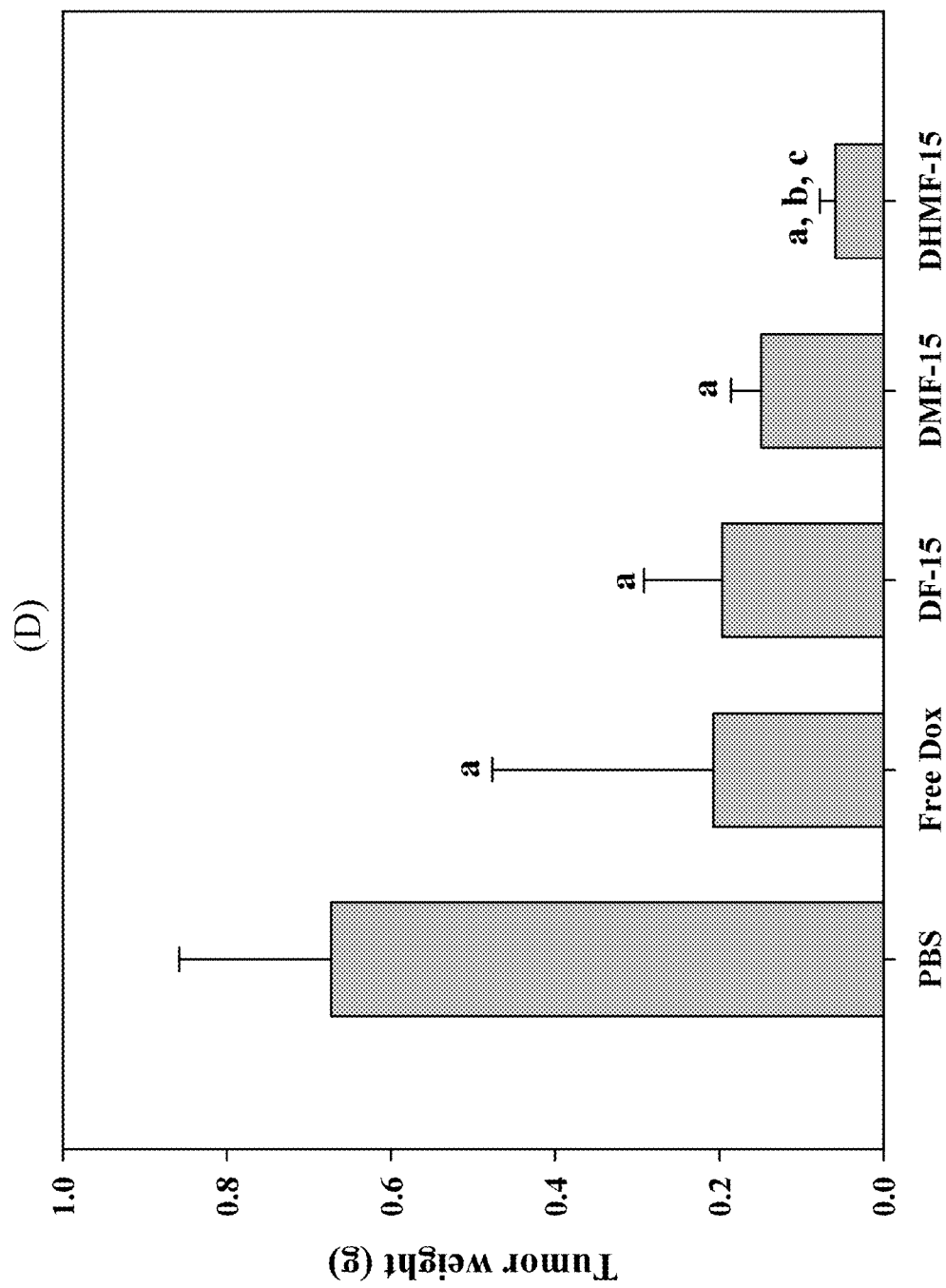

The in vivo antitumor efficacy of DHMF-15 hydrogel formulation was evaluated in the C26 tumor-bearing mice model. Mice were randomized into three groups when the tumor size reached 100 mm$^3$. Three groups of mice received intratumoral injection of PBS, DHMF-15 hydrogel, free Dox solution, DMF-15 hydrogel, and DF-15 hydrogel respectively. FIG. 9A shows the changes in tumor volumes in the C26 mice after intratumoral administration. PBS treatments had no substantial effect on C26 tumor growth, and the tumor volumes increased rapidly. After administration for 10 days, the average tumor volume in the PBS treated mice had reached over 1000 mm$^3$. The results indicate tumor size of DHMF-15 hydrogel, free Dox solution, DMF-15 and DF-15 after 10 days were 13.06%, 42.45%, 61.34%, and 72.53% of that in the PBS control group. Treatment with DHMF-15 is significantly more efficacious in tumor regression. Ranked from high to low inhibition efficacy, the formulations are ordered as follows: DHMF-15, free Dox solution, DMF-15, DF-15, PBS.

We also monitored change in body weight during the experiment as an indication of systemic toxicity. As shown in FIG. 9B showing in vivo antitumor efficacy, neither toxicity-induced death nor serious body weight loss was observed in mice after intratumoral injection with DHMF-15 hydrogel, free Dox solution, DMF-15 hydrogel and DF-15 hydrogel during the experiment.

The morphology of tumors after sacrifice of the mice is as shown in FIG. 9C. The results show the DHMF-15 hydrogel can suppress tumor growth. The tumor weights of DHMF-15 hydrogel and free Dox solution were significantly reduced compared to the control group. The tumor inhibition rate of DHMF-15 hydrogel was 84.51%, which is higher than that of free doxorubicin solution (80.65%, FIG. 9D). It can be concluded that DHMF-15 hydrogel had better tumor inhibition efficacy in the mice model, which is consistent with the in vitro cell experiment. All of the results demonstrate that DHMF-15 hydrogel not only inhibited C26 tumor growth, but also led to less systemic toxicity.

What is claimed is:

1. A thermosensitive injectable hydrogel, which has a gel formation temperature from 30° C. to 37° C. and comprises an HA polymer and a copolymer of polyethylene oxide (PEO) and polypropylene oxide (PPO), wherein the amounts of HA and the polymer are about 0.01% (w/v) to about 0.2% (w/v) and about 15% (w/v) to about 18% (w/v), respectively; wherein HA has a mean molecular weight of about 1,500,000 Da to about 2,500,000 Da.

2. The thermosensitive injectable hydrogel of claim 1, wherein HA has a mean molecular weight of 1,500,000 Da to about 2,200,000 Da.

3. The thermosensitive injectable hydrogel of claim 1, wherein the copolymer of PEO and PPO is poly(ethylene oxide-propylene oxide-ethylene oxide) (PEO-PPO-PEO).

4. The thermosensitive injectable hydrogel of claim 1, wherein the copolymer of PEO and PPO is Pluronic F68NF, Pluronic F127NF, Pluronic F108NF, Pluronic F38NF, or Pluronic F87NF.

5. The thermosensitive injectable hydrogel of claim 1, wherein the copolymer of PEO and PPO is Pluronic F127NF.

6. The thermosensitive injectable hydrogel of claim 1, which comprises about 0.01% to about 0.15% (w/v) HA and about 15% to about 17.5% (w/v) copolymer of PEO and PPO.

7. A method of using the thermosensitive injectable hydrogel of claim 1 comprising the step of administrating the thermosensitive injectable hydrogel to a subject, wherein the step is selected from the group consisting of: intratumoral injection, subcutaneous injection, oral delivery, ocular delivery, transdermal, ophthalmic, wound healing, Intraperitoneal injection, gene delivery, tissue engineering, colon specific drug delivery.

8. A drug delivery system, comprising a thermosensitive injectable hydrogel of claim 1 and an active agent.

9. The drug delivery system of claim 8, wherein the delivery is intratumoral injection, subcutaneous injection, oral delivery, ocular delivery, transdermal delivery, ophthalmic delivery, topical delivery, intraperitoneal injection, gene delivery or colon specific drug delivery.

10. The drug delivery system of claim 8, wherein the active agent is an anticancer drug, a radionuclide, a gene therapy composition, a hormone, a nutriceutical, an antibiotic, an anti-inflammatory agent, an anti-viral agent, a wound healing agent, an antibacterial agent or a combination thereof.

11. The drug delivery system of claim 10, wherein the anticancer drug is methotrexate, carboplatin, taxol, cisplatin, 5-fluorouracil, doxorubicin, etpocide, paclitaxel, camtotecin, cytosine, arabinose, docetaxel or a mixture thereof.

12. A method for treating or alleviating one or more symptoms of a disease in a subject, comprising administering to a subject in need thereof a drug delivery system of claim 8.

13. The method of claim 12, wherein the administration is intratumoral injection, subcutaneous injection, oral delivery, ocular delivery, transdermal, ophthalmic, topical delivery, intraperitoneal injection, gene delivery or colon specific drug delivery.

14. The method of claim 12, wherein the disease is a cancer.

15. The method of claim 12, wherein the drug delivery system comprises an anti-cancer drug.

16. The method of claim 15, wherein the anti-cancer drug is doxorubicin or docetaxel.

* * * * *